US011246997B2

(12) United States Patent
Benedict et al.

(10) Patent No.: US 11,246,997 B2
(45) Date of Patent: Feb. 15, 2022

(54) HANDHELD FILAMENT EXTENSION ATOMIZER FOR PRECISION DELIVERY OF DRUGS AND THERAPEUTICS

(71) Applicant: PALO ALTO RESEARCH CENTER INCORPORATED, Palo Alto, CA (US)

(72) Inventors: Michael Benedict, Palo Alto, CA (US); David Mathew Johnson, San Francisco, CA (US); Scott E. Solberg, San Jose, CA (US); Jamie Kalb, Mountain View, CA (US); Ravi Neelakantan, Redwood City, CA (US); Jerome Unidad, San Francisco, CA (US); David Charles Taylor, San Francisco, CA (US); Frances Yan, San Francisco, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 804 days.

(21) Appl. No.: 16/140,902

(22) Filed: Sep. 25, 2018

(65) Prior Publication Data

US 2020/0093998 A1 Mar. 26, 2020

(51) Int. Cl.
*B08B 3/02* (2006.01)
*A61M 11/02* (2006.01)
(Continued)

(52) U.S. Cl.
CPC ........... *A61M 11/02* (2013.01); *A61F 9/0008* (2013.01); *A61M 35/003* (2013.01); *B08B 3/02* (2013.01);
(Continued)

(58) Field of Classification Search
CPC .... A61F 9/0008; A61M 11/006; A61M 11/02; A61M 2205/07; A61M 2205/103;
(Continued)

(56) References Cited

U.S. PATENT DOCUMENTS

| | | | |
|---|---|---|---|
| 3,696,973 | A | 10/1972 | Cottell |
| 5,192,009 | A | 3/1993 | Hildebrandt et al. |

(Continued)

FOREIGN PATENT DOCUMENTS

| | | | |
|---|---|---|---|
| EP | 2 868 389 | A1 | 5/2015 |
| WO | 96/03218 | A1 | 2/1996 |

OTHER PUBLICATIONS

Ghasem, G., Nasr, Andrew J. et al., Chapter 2. Background on Sprays and Their Production, Jan. 1, 2002, Industrial Sprays and Atomization: Design, Analysis and Applications, Springer, London, Pates 7-33.

(Continued)

*Primary Examiner* — Kai H Weng
(74) *Attorney, Agent, or Firm* — Miller Nash LLP

(57) ABSTRACT

A hand-held dispenser to dispense fluid includes a casing to fit into a hand of a user, a nozzle in the casing to dispense a mist, a fluid reservoir contained in the casing to hold a fluid to be turned into the mist, a filament extension atomizer contained in the casing to generate the mist, an air source contained in the casing to provide air flow to direct the mist to the nozzle, a motor contained in the casing to operate the filament extension atomizer, an actuator positioned on the casing to activate the dispenser, a control circuit contained in the casing to receive a signal from the actuator and to send a signal to the motor to cause the motor to actuate, and a power source contained in the casing to provide power to the motor upon receive a signal from the control circuit.

35 Claims, 17 Drawing Sheets

(51) Int. Cl.
*A61F 9/00* (2006.01)
*A61M 35/00* (2006.01)

(52) U.S. Cl.
CPC . *A61M 2205/12* (2013.01); *A61M 2205/3337* (2013.01); *A61M 2205/6054* (2013.01); *A61M 2205/8206* (2013.01); *A61M 2205/8243* (2013.01); *A61M 2205/8262* (2013.01); *A61M 2209/086* (2013.01); *A61M 2209/10* (2013.01); *B08B 2203/0211* (2013.01)

(58) Field of Classification Search
CPC ...... A61M 2205/12; A61M 2205/3337; A61M 2205/3569; A61M 2205/3592; A61M 2205/6018; A61M 2205/6054; A61M 2205/8206; A61M 2205/8243; A61M 2205/8262; A61M 2209/086; A61M 2209/10; A61M 2210/04; A61M 2210/0612; A61M 35/003; B05B 12/1409; B05B 15/555; B05B 17/04; B05B 7/0012; B05B 9/0811; B05B 9/0861; B08B 2203/0211; B08B 3/02
See application file for complete search history.

(56) References Cited

U.S. PATENT DOCUMENTS

| | | | |
|---|---|---|---|
| 5,630,793 | A | 5/1997 | Rowe |
| 6,425,888 | B1 | 7/2002 | Embleton et al. |
| 2008/0054099 | A1 | 3/2008 | Giroux et al. |
| 2010/0222752 | A1 | 9/2010 | Collins et al. |
| 2017/0203326 | A1* | 7/2017 | Johnson .................. B05D 1/02 |

OTHER PUBLICATIONS http://www.optrex.co.uk/optrex-range/spray/optrex-actimist-2in1-dry-plus-irritated-eye-spray/, downloaded Apr. 3, 2019.
http://www.naturestears.com/, downloaded Apr. 3, 2019.

* cited by examiner

HANDHELD FILAMENT EXTENSION ATOMIZER FOR PRECISION DELIVERY OF DRUGS AND THERAPEUTICS

TECHNICAL FIELD

This disclosure relates to atomization of fluids, more particularly to hand-held atomizers for drug and therapeutics delivery.

BACKGROUND

The primary method for the delivery of eye drops has been an eye drop dispenser, also referred to as a droptainer. These small containers typically have an orifice with a controlled size that regulates how much liquid comes out when the container tips upside down.

However, many users find eye drops difficult to use and would welcome alternative methods to deliver materials to the eye. Additionally, since a droptainer delivers only a single drop as one large droplet, much of the volume of material delivered is lost. The delivered volume may only have 10% of the volume of the active material from the droptainer.

Spray delivery provides a method for the delivery of these drugs. Spray delivery can overcome many of the challenges associated with a droptainer since additional momentum imparted to the spray particles allows the delivery device to work at any angle relative to the eye. However, existing spray delivery systems have their own challenges. One approach, pneumatic atomization, may result in large globs of spray during the beginning of the stroke. Additionally, when non-Newtonian, extensionally hardening fluid is used a pneumatic actuator will produce a filament like stream of fluid, not a mist of small droplets. Ultrasonic and vibrating mesh technologies can produce a fine, small mist without large droplets but have extreme limitations on rheology and cannot process fluids at all that have even small amounts of extensionally hardening properties.

SUMMARY

An embodiment is a hand-held dispenser to dispense fluid includes a casing to fit into a hand of a user, a nozzle in the casing to dispense a mist, a fluid reservoir contained in the casing to hold a fluid to be turned into the mist, a filament extension atomizer contained in the casing to generate the mist, an air source contained in the casing to provide air flow to direct the mist to the nozzle, a motor contained in the casing to operate the filament extension atomizer, an actuator positioned on the casing to activate the dispenser, a control circuit contained in the casing to receive a signal from the actuator and to send a signal to the motor to cause the motor to actuate, and a power source contained in the casing to provide power to the motor upon receive a signal from the control circuit.

An embodiment is a dispensing system having a hand-held dispenser to dispense fluid as a mist. The hand-held dispenser has a casing configured to fit into a hand of a user, a nozzle in the casing arranged to dispense a mist into an eye of the user, a fluid reservoir contained in the casing to hold a fluid to be turned into the mist, a filament extension atomizer contained in the casing to receive fluid from the reservoir and to generate the mist, an air source contained in the casing, the air source to provide air flow to direct the mist to the nozzle, a motor contained in the casing, the motor connected to the filament extension atomizer to operate the filament extension atomizer, an actuator positioned on the casing to allow the user to activate the dispenser, a control circuit contained in the casing, the control circuit electrically connected to the motor and the actuator to receive a signal from the actuator and to send a signal to the motor to cause the motor to actuate, a power source contained in the casing, the power source electrically connected to the control circuit and the motor to provide power to the motor upon receive a signal from the control circuit, and a dispenser connector. The system also includes a power connector with the dispenser connector to provide power to the power source in the dispenser.

DETAILED DESCRIPTION OF THE EMBODIMENTS

Figure 1:
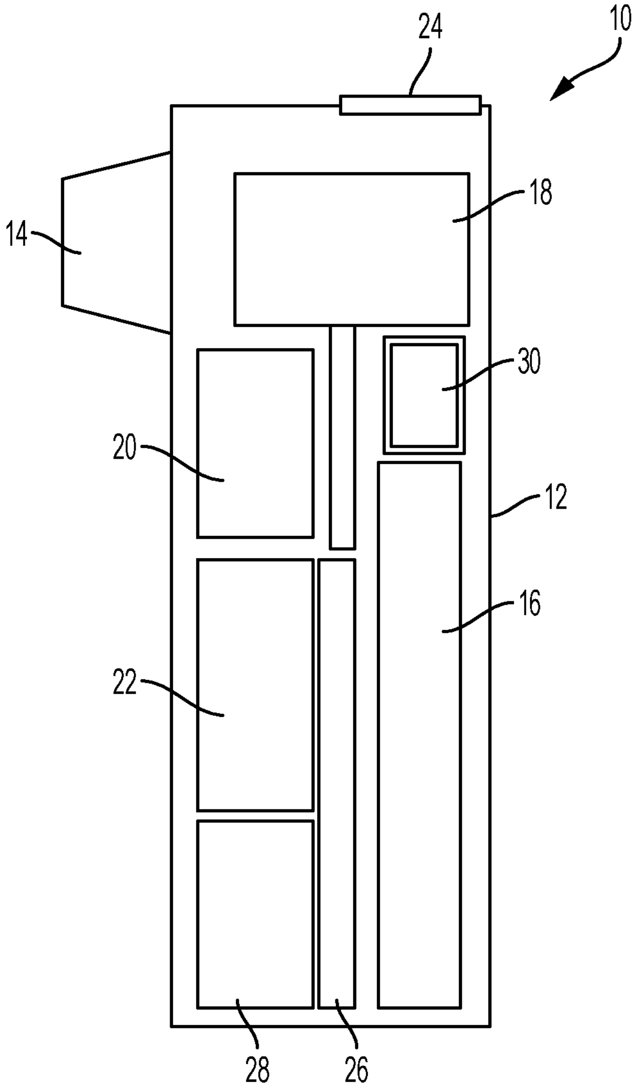
FIG. 1 shows an embodiment of hand-held fluid dispenser.

FIG. 1 shows an embodiment of a hand-held dispenser to dispense fluid as a mist using a filament extension atomizer. The hand-held dispenser has a casing 12 configured to fit in a user's hand. The casing contains all the elements of the dispenser including the nozzle 14, the liquid reservoir 16, a filament extension atomizer 18, an air source 20, a motor/drive unit 22, an actuator 24, control electronics and circuitry 26, a power source 28, and an optional flow control 30. The casing has dimensions and a form factor designed to fit into a user's hand.

The filament extension atomizer 18 receives a fluid from a fluid reservoir 16 and delivers a mist to the nozzle 14. The nozzle 14 may have a dimension selected to focus the spray on a target location of a specific size. For best results, the area is tightly controlled and as small as possible to minimize overspray, maximize delivery, and prevent undesirable contact with the skin. The fluid to be delivered may consist of some sort of therapeutic material, such as eye drops, antibiotic sprays for wounds, etc.

The fluid reservoir 16 contains the fluid. The reservoir may be refillable or replaceable, as will be discussed in more detail later. In addition, more than one reservoir may be present in the casing, with a selector knob or other means of choosing which fluid reservoir sends fluid to the filament extension atomizer. The reservoir may be pressurized, such as with air, or mechanical compression such as a spring. The liquid reservoir may interface with the filament extension atomizer and the other components of the system through a port, tube, valve, etc.

The filament extension atomizer generates a mist from the fluid under control of an electronic control circuit and powered by the motor/drive circuit 22. The air source 20 directs the mist from the filament extension atomizer to the nozzle. Since small particles (under 100 microns) are produced by the Filament Extension Atomizer, they will quickly lose momentum once they have exited the device. The air source could be an electronic air pump, a fan, a compressed container, or any other source of air volume. The air helps direct the spray towards the surface being treated and helps maximize delivery efficiency. The air speed and pressure should be minimized to maximize comfort. The choice of airflow speed and pressure may depend on the application area. For example, a close-range application, such as a range of less than 25 millimeters, requires low airspeeds to allow the maximum amount of material to reach the substrate in a small area. However, if the application uses a longer distance, the longer distance to the target will require more momentum and therefore higher air speeds. Air is activated through the use of a pump or a valve. A pump may be used if no stored air is used, in this case the pumping element is activated either through an electronic control or through the motion of the driving element to create pressure from the air. If an onboard air source is used, such as a compressed gas, the valve is actuated either through an electronic signal or the motion of the actuation drive unit to release the compressed air in a controlled manner.

The filament extension atomizer 18 converts the fluid to a mist by stretching the fluid between diverging surfaces to form filaments. The diverging surfaces cause the filaments to break up into droplets that form the mist. The filament extension atomizer may use many different types of diverging surfaces. The embodiments here employ two counter rotating rollers. As the surfaces of the rollers rotate away from each other, the fluid forms filaments that then extend to the point of breaking into a mist.

The filament extension atomizer runs under control of the motor 22. This may consist of an electric motor designed to operate at high speed, typically thousands to tens of thousands of revolutions per minute. The motor will couple to the filament extension atomizer through mechanical couplings. This could include belts, pulleys, gears, a shaft, or electrical or magnetic coupling. The filament extension atomizer may also include a gearing mechanism to drive the rollers or motors at different speeds.

The device operates when a user presses or otherwise activates the actuator 24. This may consist of a button or other actuator that causes a signal to be sent to the control electronics. For user convenience, the actuator 24 may reside in a position on the casing 12 such that the user can hold the dispenser and activate the actuator with the same hand. The button may have multiple positions or multiple sensing modes. For example, a button may initial be depressed slightly or detect contact through capacitive means to active the device's electronics or turn on some of the subsystems and then when the device is further depressed the system may dispense a dose. Alternatively, multiple sensing modes, such as capacitive and physical depressing can be used to allow two activation modes to be used.

Upon receiving a signal from the actuator, the electronic control circuitry causes the device to operate. The control circuit may control the charging of the battery or other power source 28, provide drive voltages to the motor, switch any pumps or valves, and provide user feedback and control. The electronic control circuitry may consist of a controller integrated circuit, a circuit board with the necessary components to manage the control, a field programmable gate array (FPGA), an application specific integrated circuit (ASIC), a microcontroller, etc. The actuator may actuate components either simultaneously or in a specific order. In some embodiments, the air is turned on first, followed by a short delay, the motor is activated to turn on the rollers, after another short delay the pump is activated for a fixed period of time. When the pump has been deactivated, the motor is turned off, followed by a short delay, followed by the airflow.

The electronics may include a communications link to allow the dispenser to communicate with device external to the dispenser through common wireless protocols such as Bluetooth, WiFi, or other near-field communications. The battery 28 will typically consist of a rechargeable battery and may be charged by a cord, contacts, or a wireless inductive charging system.

FIG. 1 also shows a pump/flow control module 30 that may control the dosing of the liquid. This may include a pump or other means of flow control, such as a piezoelectric pump, under control of the electronic control circuitry. The pump may be optional, however, if the reservoir is pressurized. The dosing would be controlled by a valve instead of the pump. The air source previously described can also be utilized to provide a driving pressure to the reservoir with control being achieved by a valve.

Figure 2:
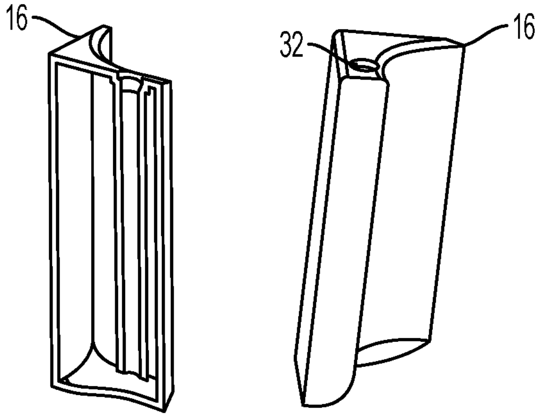
FIG. 2 shows an embodiment of a replaceable cartridge for a hand-held fluid dispenser.
Figure 3:
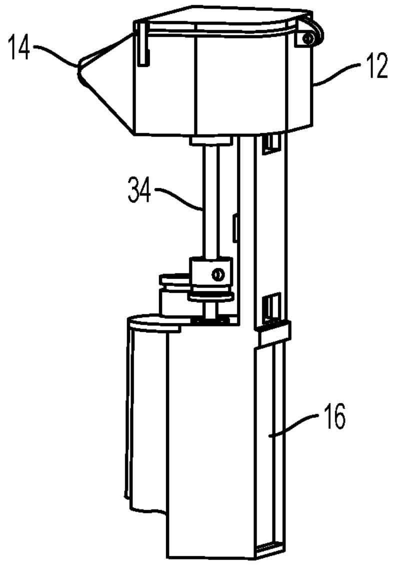
FIGS. 3 and 4 show embodiments of a hand-held fluid dispenser with a replaceable fluid cartridge.
Figure 4:
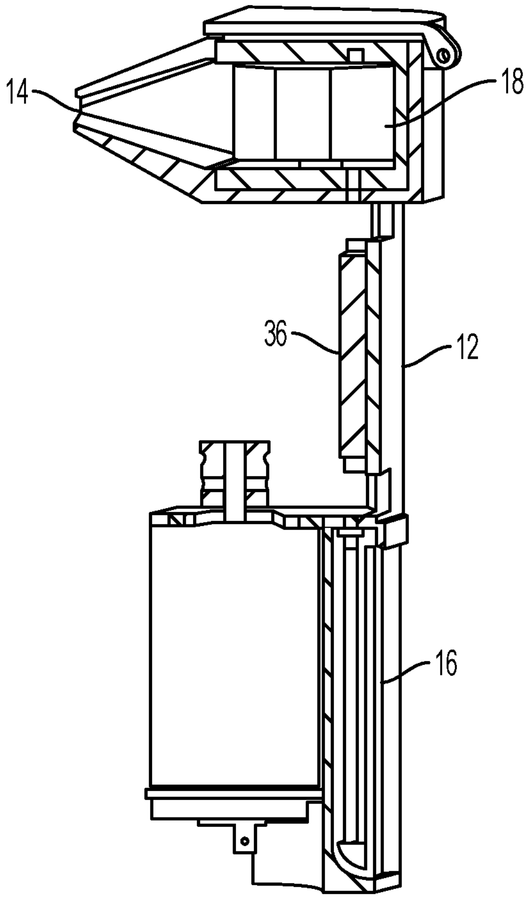

The dispenser shown in FIG. 1 allows the user to easily and accurately dispense a mist of fluid onto a target area. To make the dispenser more convenient for the user, as well as ensuring the proper operation of the device, some of the components may be replaceable. FIGS. 2-4 show an embodiment of a dispenser in which the fluid reservoir 16 consists of a replaceable fluid cartridge. As shown in FIG. 2, the fluid cartridge may include a valve/seal 32. In one embodiment, the seal may have a breakable inner surface that a structure or tube on the dispenser will break. The inner seal protects the contents of the cartridge from external contamination when the cartridge is not loaded. A seal ring then forms a liquid tight seal with the cartridge to avoid leakage and contamination. The seal structure may also include a valve that the control electronics can actuate. This may operate similarly to inkjet cartridges that have a small electrically-controlled valve that opens to allow ink to exit the inkjet cartridge and fall on paper or other print substrate.

The fluid cartridge my contain multiple fluids simultaneously, separated by air or by a barrier of some kind, such as a film. As the device dispenses the fluid, it eventually exhausts all the therapeutic or drug fluid. The device will then reach the cleaning fluid and dispense cleaning fluid, cleaning the system. The user may be notified that is reaching the end of the useable fluid and cleaning fluid is about to be dispensed, by counting the number of doses dispensed from a cartridge or by detecting a change in the fluid, such as viscosity, optical opacity, or viscosity.

Additionally, a fluid cartridge may contain multiple chambers separated by a divider. The divider may be a film or a solid wall. A cartridge will multiple chambers will include multiple seal and puncture structures and the device itself may have multiple valves or pumps to accommodate the multiple fluids. In this manner, the system may select from multiple fluids to dispense. For example, if a treatment involves multiple drugs, the system may dispense them sequentially to the user. Alternatively, one chamber may be a cleaning solution that the user can choose to activate if the device needs to be cleaned.

The system may have multiple means for detecting information about the cartridges that have been loaded. A RFID or NFC tag can be placed on the cartridge in the form of a label or as a small component. The system electronics can be configured with electronics to read this data using the appropriate wireless protocols to detect information about the cartridge inserted. The information can include things like the material contained within the cartridge, the amount of fluid or doses, dose amount settings, settings for the FEA system, serial number, expiration date, or the recommended dose frequency for the user. The system can use this data to adjust settings of the airflow and the FEA spray system or provide information or prompts to the user to use the fluid at a certain frequency or time.

FIGS. 3 and 4 show different options for the configuration of the dispenser. In FIG. 3, the pump is used and has a drive shaft 34 that pumps the fluid from the reservoir to the filament extension atomizer. In FIG. 4, typically with a pressurized container, only a conduit 36 is needed to transport the fluid from the reservoir to the filament extension atomizer 18.

Figure 5:
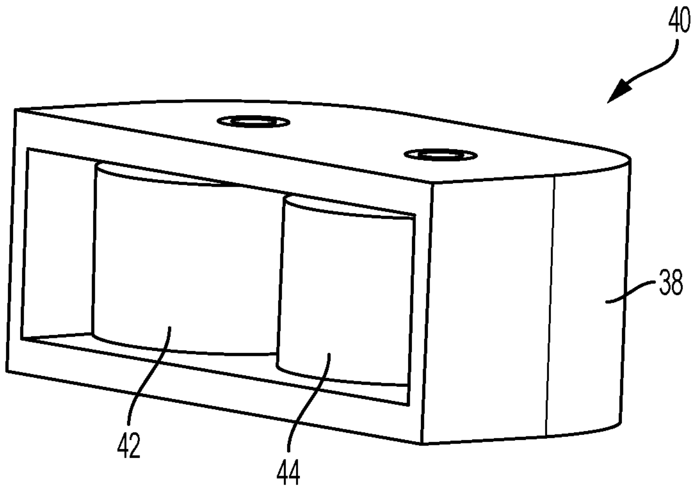
FIGS. 5 and 6 show an embodiment of a replaceable head cartridge for a hand-held fluid dispenser.

In addition to replaceable fluid cartridges, other components may be replaceable, including the filament extension atomizer rollers. These removable cartridges, referred to here as head cartridges, contain the rollers. FIGS. 5-9 show embodiments of replaceable head cartridges. In FIG. 5, the head cartridge system 40 contains the counter-rotating rollers 42 and 442 enclosed by head cartridge casing 38, referred to here as the head cartridge. This casing can be removed as a single unit and can easily be replaced. The head cartridges may have a communications link, such as NFC or RFID that allows the head cartridge to send information to the dispenser or one or more external devices, as discussed with regard to the cartridges above.

Figure 6:
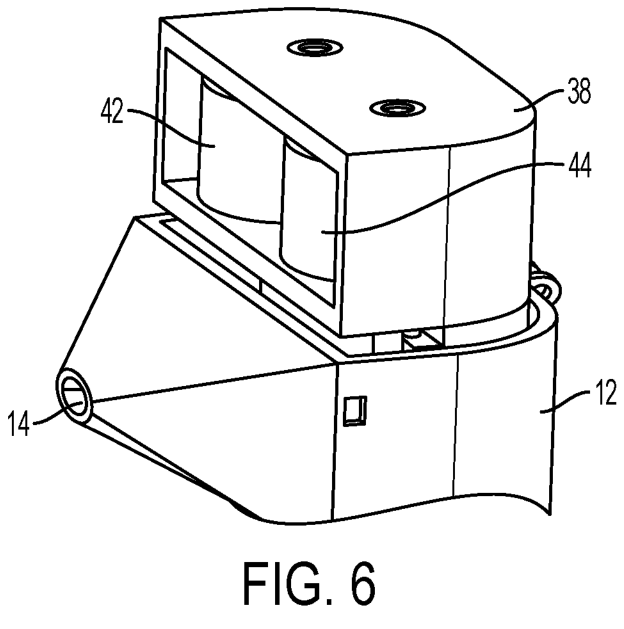
Figure 7:
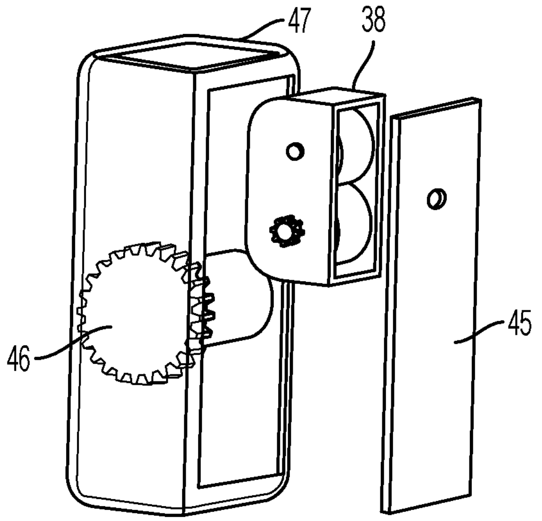
FIGS. 7 and 8 show an alternative embodiment of a replaceable head cartridge for a hand-held dispenser.
Figure 8:
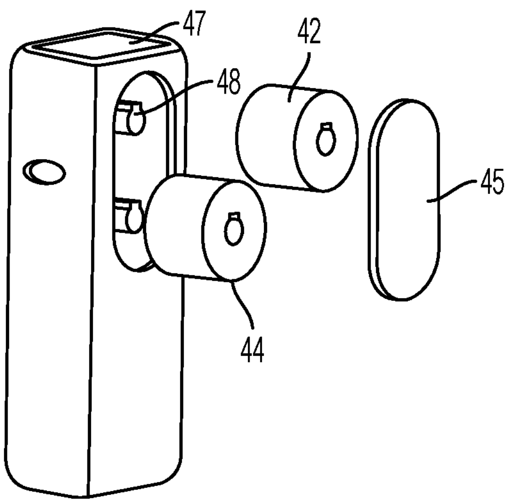
Figure 9:
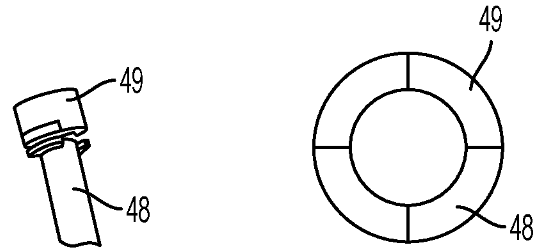
FIGS. 9-11 show various embodiments of drive shafts for a replaceable head cartridge.
Figure 10:
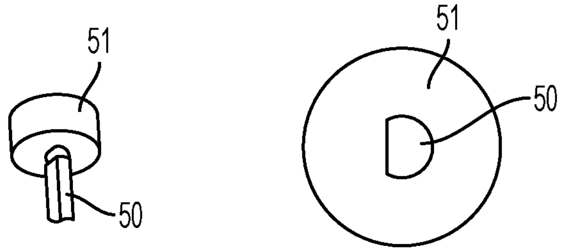
Figure 11:
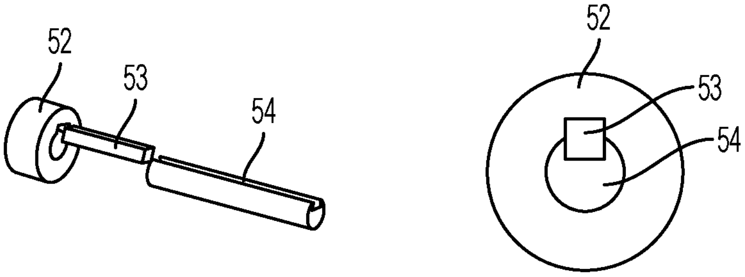

FIG. 6 shows the replaceable head cartridge 38 in a horizontal arrangement that drops into the casing 12 to allow the rollers 42 and 44 to provide mist to the nozzle 14. FIGS. 7 and 8 show a replaceable head cartridge with the rollers 42 and 44 in a vertical orientation. In this embodiment, the case 47 has an opening and a cover 45. The head cartridges 38 slides into the opening and then the cover is closed. In this embodiment, a gear or spline 46 of FIG. 7 matches with a gear on the head cartridge to provide driving force for the rollers. FIG. 8 shows a similar vertical arrangement, but the drive force is supplied by shafts. FIGS. 9-11 show other options for drive connections.

Figure 12:
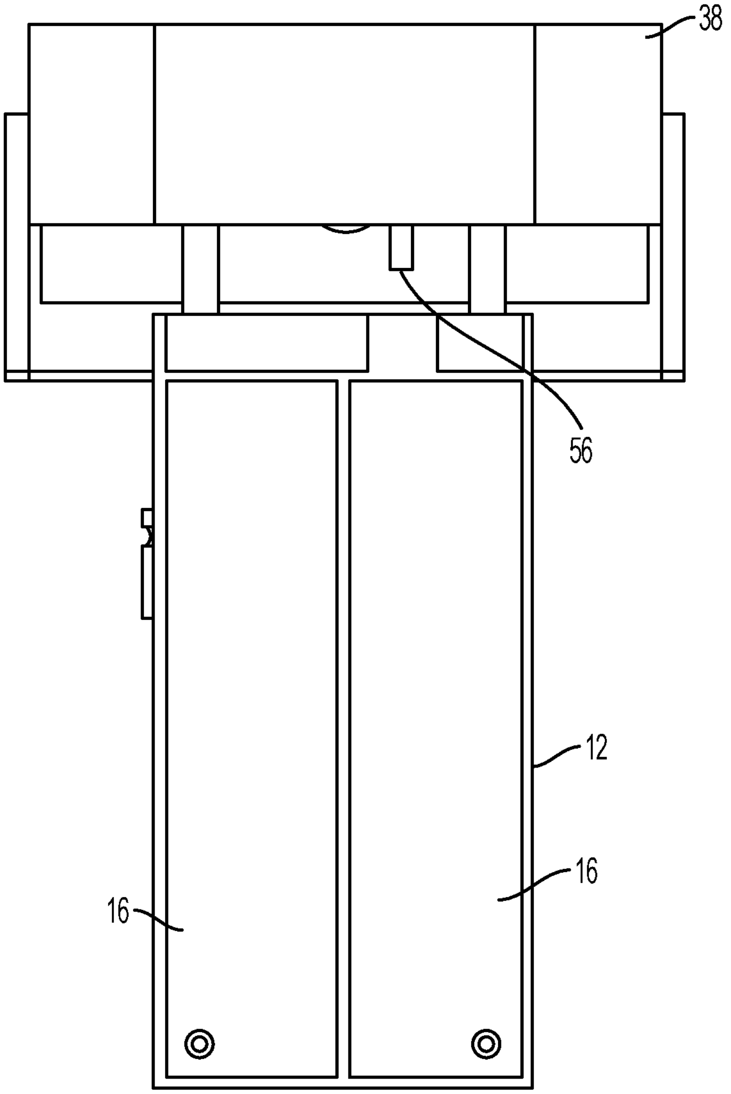
FIG. 12 shows an embodiment of a replaceable head cartridge having connection tubes.

FIG. 9 shows a side view and a top view of a shaft 48 and its coupler 49. FIG. 10 shows a d-shaped shaft 50 and its coupler 51. FIG. 11 shows an example of a keys/keyway set up of the slot 54, the key 53 and their coupler 52. When the head cartridges connect to the dispenser, the connection needs to be a leak-resistant hydraulic connection. FIG. 12 shows a coupling tube 56 that snaps into the right reservoir 16 to allow transport of the fluid from the right reservoir 16. The left reservoir may have a different coupling tube, not shown, to allow the user to select from different fluids.

The rollers, in either the replaceable cartridge or not, have a similar size to the motor size. It is possible to utilize what is commonly referred to as a "hub motor" to combine the motor and roller subsystems. In this implementation the rotor is the roller and the stator is internal to the roller. The motor may consist of many different constructions, but a typical form would be a brushless DC motor with a permanent magnet (PM) rotor.

Figure 13:
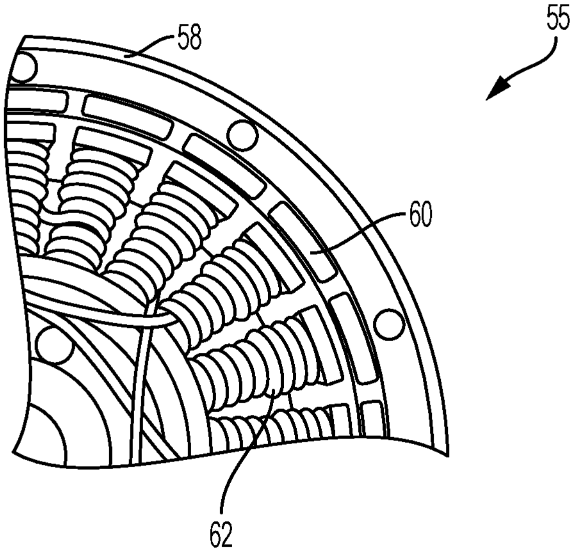
FIG. 13 shows an embodiment of a filament extension atomizer roller having a hub motor.

FIG. 13 shows an embodiment of a hub motor 55. The array of permanent magnets resides internal to the roller. The hub would have an electromagnetic stator, and there would be a bearing which puts the hub and roller/rotor in rotating mechanical communication. FIG. 13 shows a quarter section of this embodiment. The roller may have a coating or outer surface 58. The permanent magnet array/rotor 60 resides inside the roller towards the outer edge, and the stator hub 62 resides inside the array of magnets. The outer surface 58 may be detachable from the rest of the assembly in an easy manner. This material may be replaced by the user or replaced by a professional service on a regular basis.

Figure 14:
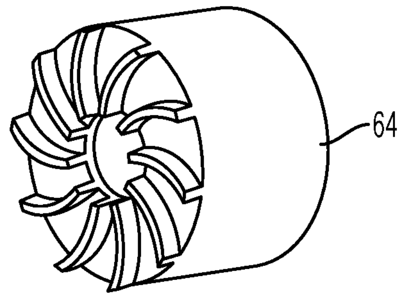
FIG. 14 shows an embodiment of an impeller attachable to a motor in a hand-held fluid dispenser.

The rollers rotate at speeds like many fans and blowers and have a similar diameter. Generation of a pressure differential directly on the surface of the rollers can induce air flow useful for the filament extension atomizer. One embodiment includes an impeller feature directly onto the radial face of the roller to create tangential air flow as shown with the impeller 64 of FIG. 14.

Figure 15:
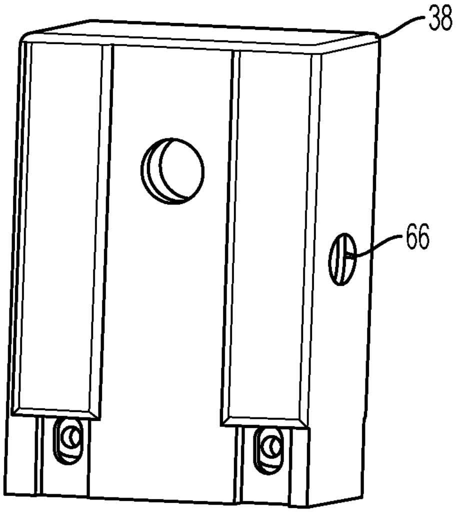
FIGS. 15 and 16 show an embodiment of a casing and internal rollers for a hand-held fluid dispenser.
Figure 16:
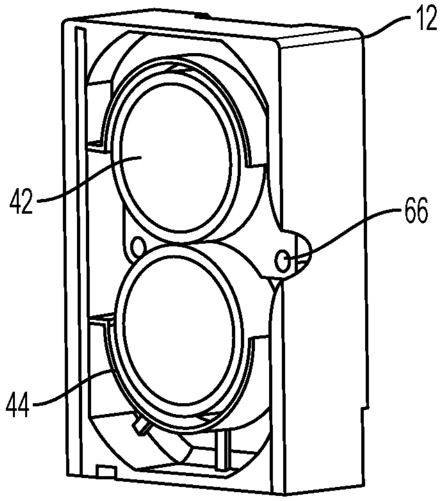
Figure 17:
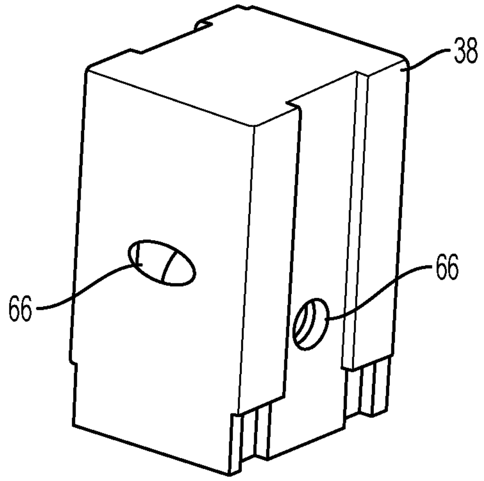
FIGS. 17 and 18 show an embodiment of a casing, internal rollers, and an impeller for a hand-held fluid dispenser.
Figure 18:
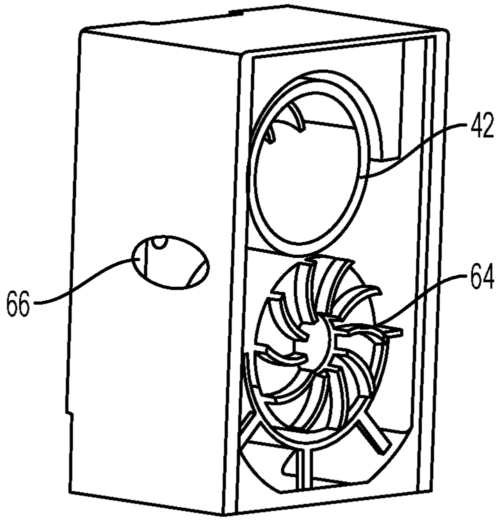

In this embodiment, the impeller pulls air in near the axis of rotation of the roller and blows it tangentially outwards in the radial direction. The filament extension atomizer may have additional features to direct the air both into the roller/blower and out of the tangential blades to create useful air flows. FIGS. 15 and 16 show external and internal views of the roller casing 38 containing the internal motors, combined roller blowers 42 and 44, and air flow features on the filament extension atomizer system. The case 38 has air holes such as 66 to provide for air flow. FIGS. 17 and 18 show external and internal views of another embodiment of a casing 38 having external holes such as 66, and the internal rollers such as 42, one of which has an impeller 64.

Figure 19:
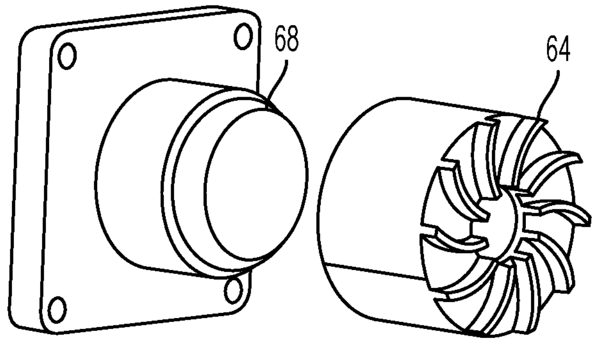
FIG. 19 shows an embodiment of a motor mount and a mountable impeller for a hand-held fluid dispenser.
Figure 20:
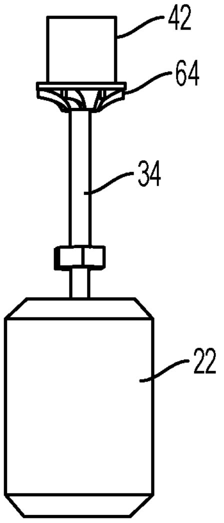
FIG. 20 shows an embodiment of a drive shaft having shared but separated roller and air generating components.

FIG. 19 shows an impeller 64 mountable to the motor stator 68, providing a system where the rollers and air generation system are easily replaceable. The roller and impeller can be removed and reattached the motor stator to facilitate cleaning or to be replaced. FIG. 20 shows an alternative arrangement where the motor 22 has a common shaft 34 with the roller 42, and a separate impeller 64. Alternatively, the impeller can be mounted on a separate shaft, connected to the motor through a coupling but not connected to the same drive shaft as the rollers. This may allow the impeller to operate at speeds other than the same speed as the roller, which will allow for airspeed and pressure to be modulated separately.

The use of a motor may allow the system to track the cleanliness of the rollers. The solution may leave behind a sticky polymer residue which becomes especially thick at the nips, where the rollers meet. These areas may have enough sticky material to affect the operation of the motors. This can be used to detect over-current, although other methods could be used.

Figure 21:
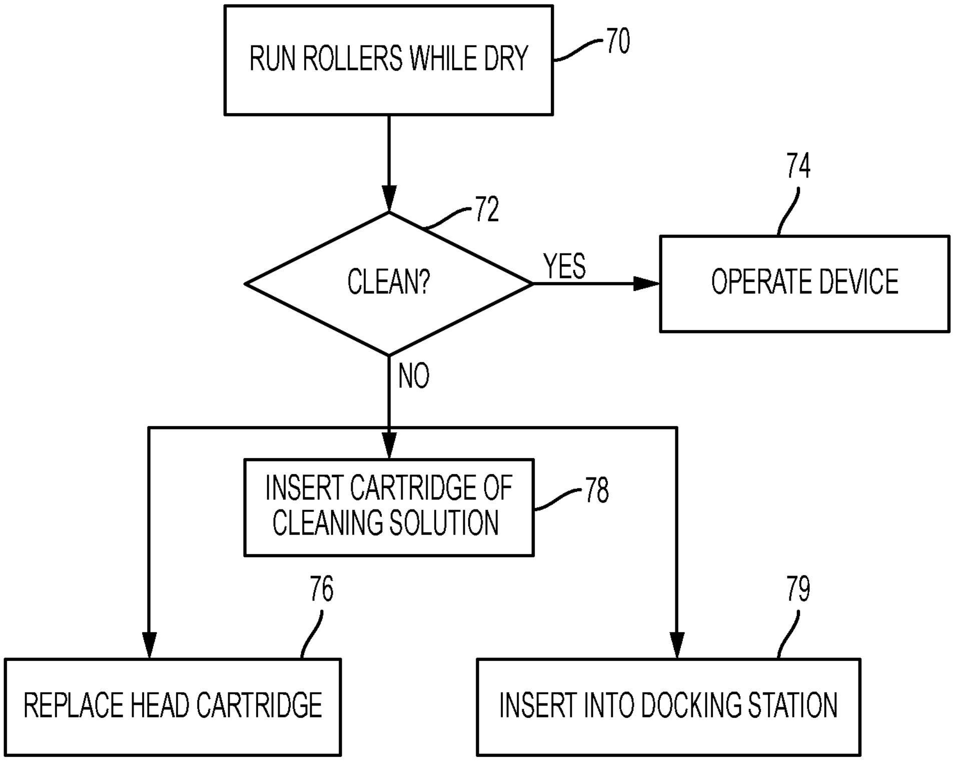
FIG. 21 shows a flowchart of an embodiment of a cleaning process for a dispensing device.

FIG. 21 shows one embodiment of a method to monitor the cleanliness of the rollers. At 70, the rollers would be run 'dry' with no product solution to determine if they are 'sticky.' The motor current or speed would be monitored, and the system microcontroller would be programmed to determine if the rollers are ready to be used for a spray run using product solution at 72. If the rollers are clean and ready to run, the operation of the device is allowed at 74. If they are not ready to be run, the user would be directed to clean the rollers.

Cleaning the rollers may involve replacing the rollers, as in the head cartridge replacement discussed above at 78, the user can insert the roller into a cleaning/docking station to allow the rollers to be cleaned at 79, or the user could insert a cartridge of cleaning solution into the dispenser to clean the rollers with a cleaning solution.

A docking station may be used for other reasons, such as charging, storage, etc., but it can also be used to clean the dispenser. FIGS. 22-27 show embodiments of a docking/cleaning station showing various configuration and locations of the cleaning solution. In FIGS. 22-27, the docking station 80 receives the dispenser casing 12. The dispenser casing has the reservoir 16, the battery and electronics 26 and 28, shown here as the battery 28, and the rollers such as 42. The docking station 80 has station electronics 82, which will typically include a recharging point for the dispenser, either by a connector, contact pads, or an inductive charging system. The docking station will connect to wall power at 88, typically an alternative current source. The docking station will also include a cleaning reservoir 84 of cleaning solution and a waste collection area 86.

Figure 22:
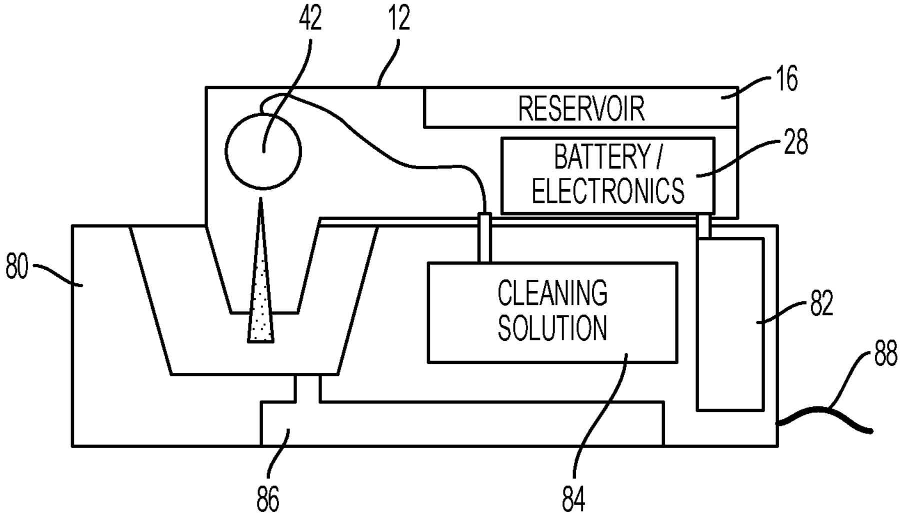
FIGS. 22-27 show embodiments of a docking and cleaning station for a hand-help fluid dispenser.

FIG. 22 shows a configuration in which the cleaning solution enters the device from the front side of the device. An internal flow channel directs the flow to the rollers where the fluid is dispensed onto the rollers. The fluid may be dispensed similar to the manner in which the fluid is dispensed during spray operation. The docking station, which can communicate the device, either wirelessly or through the electrical contacts, may activate the rollers to clean them. The rollers may spin faster, slower, or the same rate as it would during spray operation based on the cleaning solution being used. In one embodiment, saline solution is used and the rollers spin at a faster rate. The cleaning solution cleans not just the rollers, but is dispersed along the entire nozzle and cleans the inside surface.

Figure 23:
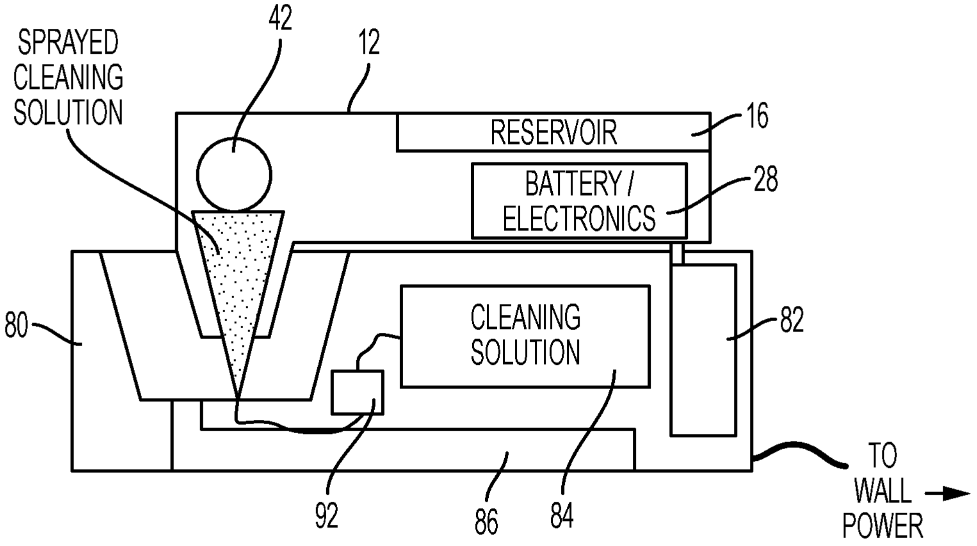

In FIG. 23, the cleaning solution is sprayed up into the front side of the rollers by pump 92, or the rollers may spin, and the solution then runs down into the waste collection area 86.

Figure 24:
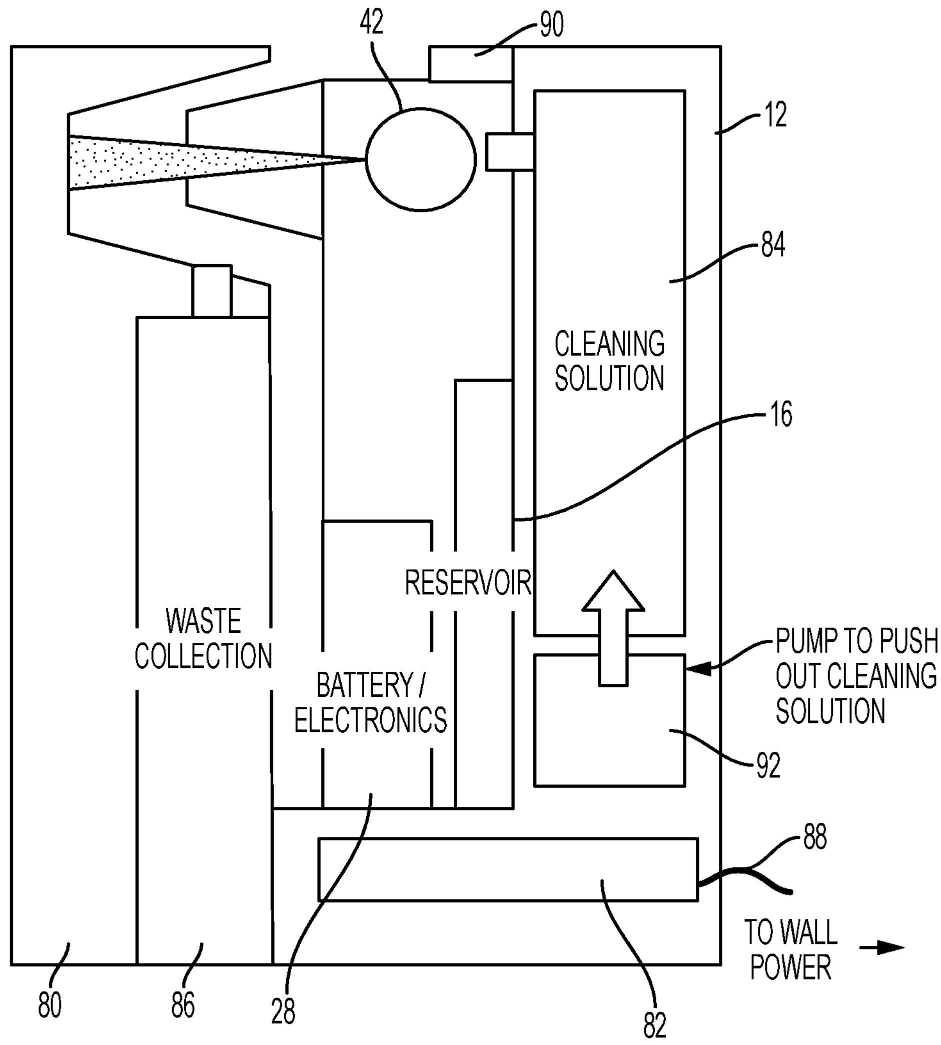

FIG. 24 shows another alternative, where the dispenser 'snaps' into the cleaning station and held in place by a latch or magnet 90. A pump 92 pumps the cleaning solution up to the back side of the rollers. The rollers are activated and spun at very high speed to propel the cleaning solution towards the cleaning station 80. After hitting the back wall of the cleaning station, the excess fluid runs down the system to the waste collection area 86.

Figure 25:
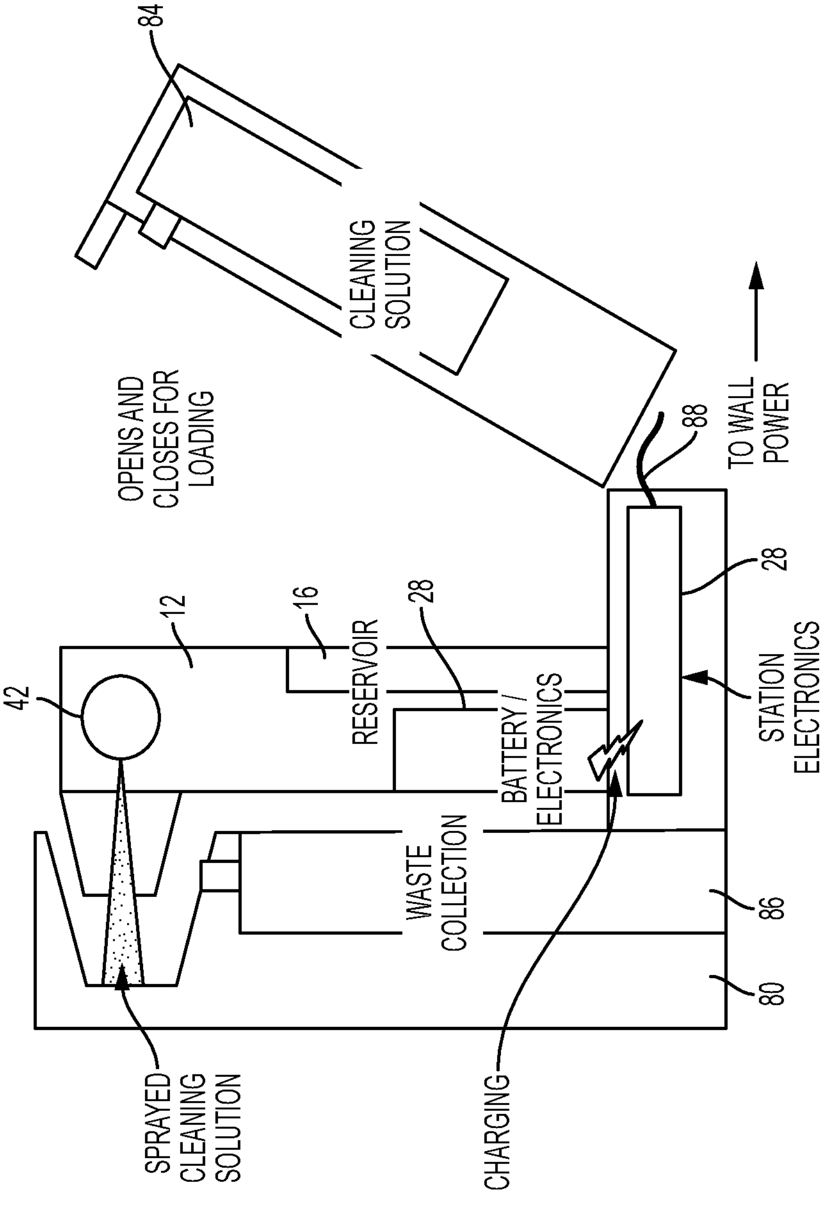

FIG. 25 shows an embodiment of the docking station in which the station opens to allow the dispenser to be inserted and then the cleaning solution reservoir closes behind it to allow the cleaning solution to be attached to the back side of the dispenser. In this embodiment the cleaning solution is pressurized to allow the cleaning solution to be sprayed onto the rollers.

Figure 26:
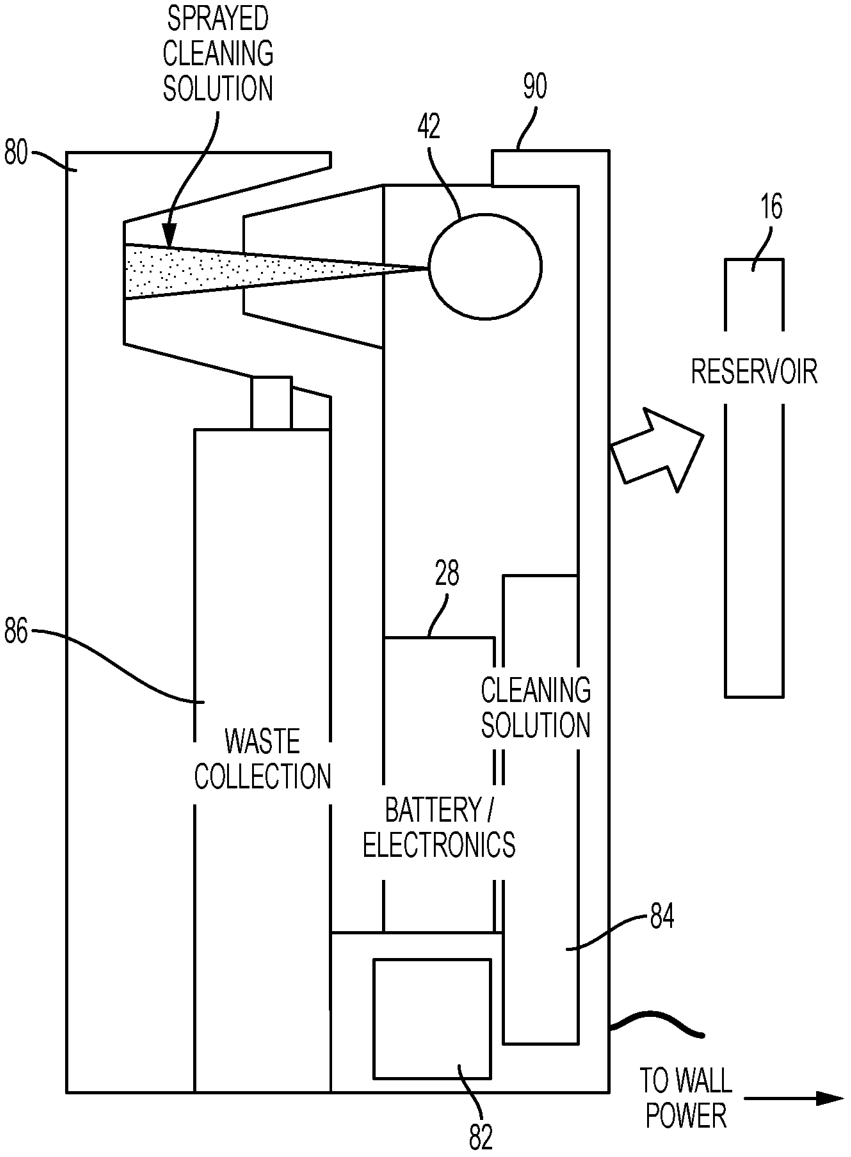

FIG. 26 shows an embodiment in which the product fluid reservoir is removed and the device is docked with the cleaning station which includes a feature that mates into the replaceable cartridge hole. Through this mating, it can run cleaning solution through the entire system. The mated feature may be the same size and design as a cartridge or may be significantly larger, only designed to replicate the mating features of the cartridge. The cleaning solution is moved through the system by the pump inside the device, activated by the cleaning station. The cleaning solution is sprayed or dispersed by the rollers when they are activated and fluid is dispensed onto them. The dispenser has contacts or an inductive charging system in the station electronics 82.

Figure 27:
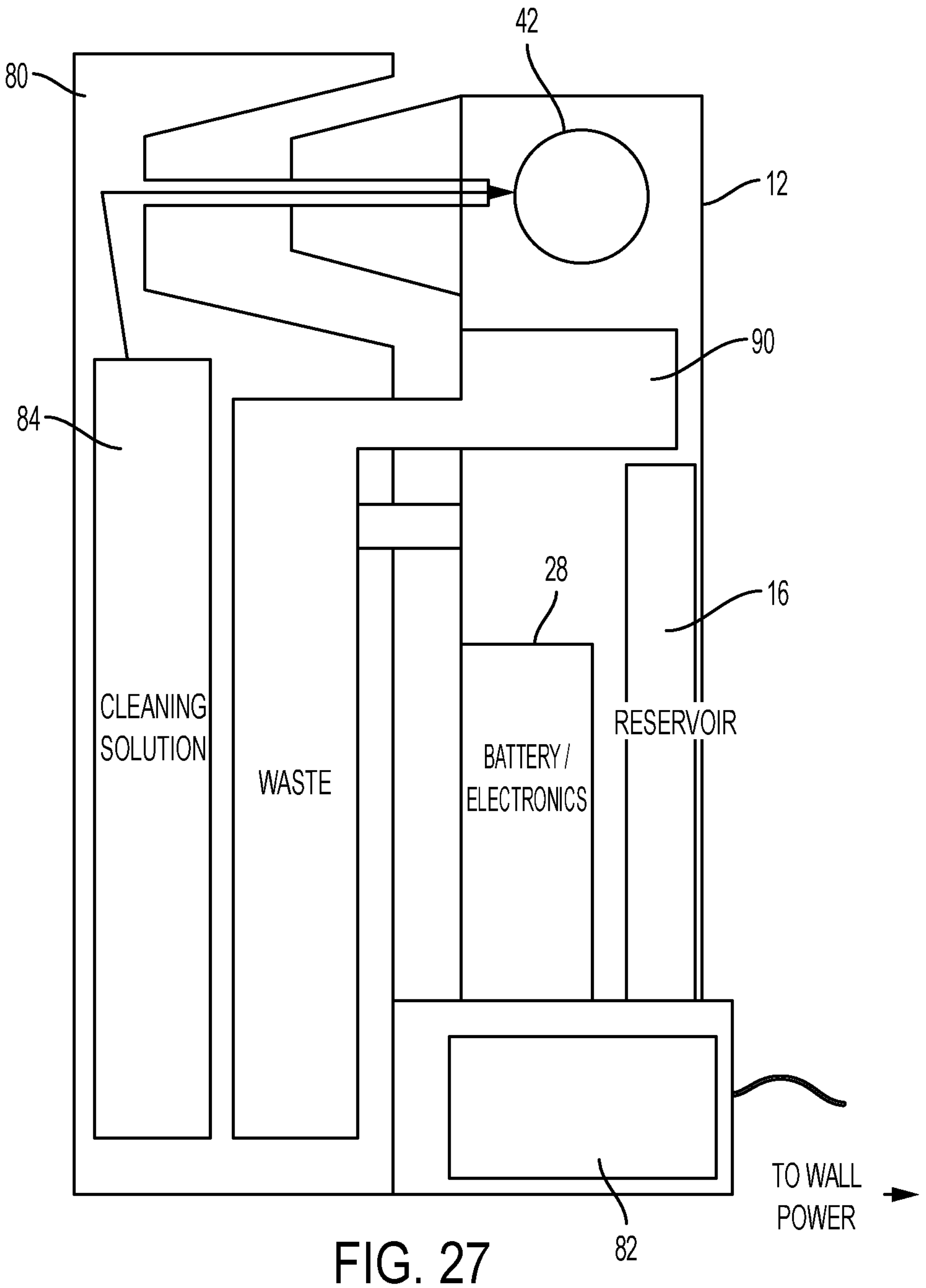

FIG. 27 shows another embodiment, in which the cleaning solution resides in the docking station and sprays on the front side of the rollers. A magnet or a latch 92, as shown in FIGS. 24 and 26 is included in the docking station and the device itself. The two parts are designed to mate with each other such that the device is attached to the docking station, but can be removed by the user when cleaning or charging is complete. A tube is included that sprays the solution at a distance close to the rollers themselves. The rollers may be activated so that the material is sprayed or dispersed throughout the device and eventually onto the station itself. The solution then goes into an internal waste collection reservoir connected to the other waste collection area. Any of these docking stations will allow the rollers to be cleaned to allow better operation of the dispenser.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A hand-held dispenser to dispense fluid as a mist, comprising:

a casing configured to fit into a hand of a user;

a nozzle in the casing arranged to dispense a mist;

a fluid reservoir contained in the casing to hold a fluid to be turned into the mist;

a filament extension atomizer contained in the casing to receive fluid from the fluid reservoir and to generate the mist;

an air source contained in the casing, the air source arranged adjacent the filament extension atomizer to provide air flow to direct the mist to the nozzle;

a motor contained in the casing, the motor connected to the filament extension atomizer to operate the filament extension atomizer;

an actuator positioned on the casing to allow the user to activate the dispenser;

a control circuit contained in the casing, the control circuit electrically connected to the motor and the actuator to receive a signal from the actuator and to send a signal to the motor to cause the motor to actuate; and a power source contained in the casing, the power source electrically connected to the control circuit and the motor to provide power to the motor upon receive a signal from the control circuit.

2. The dispenser of claim 1, further comprising a pump connected to the fluid reservoir and the filament extension atomizer to move fluid from the fluid reservoir to the filament extension atomizer.

3. The dispenser of claim 1, wherein the fluid reservoir is pressurized, the fluid reservoir having a control valve to control an amount of fluid to be dispensed.

4. The dispenser of claim 1, wherein the filament extension atomizer comprises a pair of counter-rotating rollers, the rollers arranged to receive the fluid and generate a mist from the fluid by stretching the fluid between diverging surfaces of the rollers.

5. The dispenser of claim 4, wherein the rollers are contained within a replaceable head cartridge.

6. The dispenser of claim 5, wherein the replaceable head cartridge has alignment features to allow the user to properly align the replaceable head cartridge to ensure mating of power connections and any seals.

7. The dispenser of claim 5, wherein the replaceable head cartridge includes at least one of a fluid-tight seal and an air-tight seal.

8. The dispenser of claim 5, wherein the replaceable head cartridge includes at least one sensor and a communications link to the dispenser.

9. The dispenser of claim 1, wherein the air source comprises one of an electronic air pump, a fan, and a compressed air container.

10. The dispenser of claim 1, wherein the control circuit is configured to control the power source, provide drive voltages to devices within the casing, switch operating modes for devices within the casing, provide user feedback, to receive an actuation signal from the actuator and cause the dispenser to operate.

11. The dispenser of claim 1, wherein the fluid reservoir comprises at least one of a refillable reservoir or replaceable cartridge.

12. The dispenser of claim 11, wherein the replaceable cartridge includes a seal that is breakable by a structure on the casing when the replaceable cartridge is inserted into the casing.

13. The dispenser of claim 11, wherein the replaceable cartridge includes a permanent seal having alignment features such that the permanent seal will align in the casing to prevent leakage.

14. The dispenser of claim 11, wherein the replaceable cartridge includes at least one sensor and a communication link to the dispenser.

15. The dispenser of claim 1, wherein the fluid reservoir comprises multiple fluid reservoirs, each fluid reservoir having a different fluid.

16. The dispenser of claim 1, wherein the actuator comprises a button.

17. The dispenser of claim 1, wherein the actuator is arranged on the casing to allow the user to activate the actuator with a same hand holding the dispenser.

18. The dispenser of claim 4, wherein the motor comprises a hub motor having one of the rollers as a rotor.

19. The dispenser of claim 18, wherein the rotor comprises a roller with an array of permanent magnets attached internally and the motor having a stator internal to the roller.

20. The dispenser of claim 1, wherein the air source comprises an impeller feature to generate air flow.

21. The dispenser of claim 1, further comprising a communications link to allow the dispenser to send information to an external system.

22. The dispenser of claim 5, wherein the control circuit is operable to:
- provide power to the rollers and rotate them prior to application of any product fluid;
- monitoring the motor to determine if the rollers are contaminated;
- communicating with the user when the rollers are contaminated.

23. The dispenser of claim 22, wherein communicating with the user comprises informing the user that the rollers need to be one of cleaned or replaced.

24. The dispenser of claim 22, wherein communicating with the user comprises informing the user that the rollers need to be cleaned and dispensing cleaning solution on the rollers to clean them.

25. A dispensing system, comprising:
- a hand-held dispenser to dispense fluid as a mist, comprising:
  - a casing configured to fit into a hand of a user;
  - a nozzle in the casing arranged to dispense a mist into an eye of the user;
  - a fluid reservoir contained in the casing to hold a fluid to be turned into the mist;
  - a filament extension atomizer contained in the casing to receive fluid from the fluid reservoir and to generate the mist;
  - an air source contained in the casing, the air source to provide air flow to direct the mist to the nozzle;
  - a motor contained in the casing, the motor connected to the filament extension atomizer to operate the filament extension atomizer;
  - an actuator positioned on the casing to allow the user to activate the dispenser;
  - a control circuit contained in the casing, the control circuit electrically connected to the motor and the actuator to receive a signal from the actuator and to send a signal to the motor to cause the motor to actuate;
  - a power source contained in the casing, the power source electrically connected to the control circuit and the motor to provide power to the motor upon receiving a signal from the control circuit; and
  - a dispenser connector; and
- a power connector configured to connect with the dispenser connector to provide power to the power source in the dispenser.

26. The dispensing system of claim 25, wherein the power connector comprises one of a power cord, power contacts or a wireless induction connector.

27. The dispensing system of claim 25, wherein the power connector resides in a docking station.

28. The dispensing system of claim 27, wherein the docking station includes a cleaning station to clean the filament extension atomizer of the dispenser when needed.

29. The dispensing system of claim 28, wherein the cleaning station comprises:
- a housing to house components of the cleaning station;
- station electronics arranged to connect with the control circuitry and the power source of the dispenser when the dispenser is docked in the cleaning station;
- a cleaning reservoir of cleaning solution;
- a waste collection reservoir to collect cleaning solution after the cleaning solution has been applied to the filament extension atomizer to clean the filament extension atomizer; and
- a power connection to an alternating current power source.

30. The dispensing system of claim 29, wherein a conduit for the cleaning solution couples to a back side of the filament extension atomizer to spray cleaning solution through the filament extension atomizer as the filament extension atomizer operates.

31. The dispensing system of claim 29, wherein a conduit for the cleaning solution couples to a front side of the filament extension atomizer to spray cleaning solution towards the front side of the filament extension atomizer.

32. The dispensing system of claim 28, wherein the cleaning station is configured to open to allow insertion of the dispenser into the cleaning station.

33. The dispensing system of claim 29, wherein the housing has a latching mechanism to latch the dispenser into place in the cleaning station.

34. The dispensing system of claim 29, wherein the cleaning reservoir of cleaning solution comprises a cartridge to replace the fluid reservoir in the dispenser.

35. The dispensing system of claim 29, wherein the waste collection reservoir is arranged to receive waste fluid from inside the dispenser.

* * * * *